US008962516B2

(12) United States Patent
Bergens et al.

(10) Patent No.: US 8,962,516 B2
(45) Date of Patent: Feb. 24, 2015

(54) HETEROGENEOUS RHODIUM METAL CATALYSTS

(75) Inventors: Steven H. Bergens, Edmonton (CA); Andrew Douglas Sullivan, Calgary (CA); Michael Hass, Edmonton (CA)

(73) Assignee: The Governors of the University of Alberta, Edmonton, Alberta, CA (US)

( * ) Notice: Subject to any disclaimer, the term of this patent is extended or adjusted under 35 U.S.C. 154(b) by 398 days.

(21) Appl. No.: 13/498,853

(22) PCT Filed: Sep. 28, 2010

(86) PCT No.: PCT/CA2010/001547
§ 371 (c)(1),
(2), (4) Date: Sep. 10, 2012

(87) PCT Pub. No.: WO2011/035445
PCT Pub. Date: Mar. 31, 2011

(65) Prior Publication Data
US 2013/0053576 A1    Feb. 28, 2013

Related U.S. Application Data

(60) Provisional application No. 61/246,166, filed on Sep. 28, 2009.

(51) Int. Cl.
C07D 207/12 (2006.01)
B01J 27/13 (2006.01)
B01J 23/46 (2006.01)
C07F 15/00 (2006.01)
C07B 53/00 (2006.01)
C07D 307/28 (2006.01)
C07D 403/10 (2006.01)
C07F 9/572 (2006.01)

(52) U.S. Cl.
CPC ............... *C07F 15/008* (2013.01); *C07B 53/00* (2013.01); *C07D 307/28* (2013.01); *C07D 403/10* (2013.01); *C07F 9/5728* (2013.01)
USPC .......................................... 502/230; 548/402

(58) Field of Classification Search
None
See application file for complete search history.

(56) References Cited

U.S. PATENT DOCUMENTS 6,992,201 B2 * 1/2006 Scholz et al. ................... 556/20

OTHER PUBLICATIONS

Ralph, et al., Organometallics, 26:1571 (2007).*
First Office Action for Chinese Patent Application No. 201080042121.2 dated Aug. 30, 2013.
PCT International Preliminary Report on Patentability and Written Opinion for PCT/CA2010/001547 dated Apr. 12, 2012 (6 pages).
International Search Report for PCT/CA2010/001547 mailed Jan. 14, 2011.
Dragutan, V., et al., "Metathesis catalyzed by the platinum group metals.", *Platinum Metals Review*, Jul. 1, 2000, vol. 44, No. 3, pp. 112-118.
Zhang, Z., et al., "Transition Metal-Catalyzed Intramolecular Enyne Cyclization Reaction," *Current Organic Chemistry*, 2006, vol. 10, No. 12.
Office Action for Japanese patent application 2012-530065 mailed Mar. 18, 2014 (including English summary).
Second Office Action for Chinese patent application 2010800421212 mailed Jul. 1, 2014 (including English translation).
Somanathan, R., et al., "Immobilized Chiral Metal Catalysts for Enantioselective Hydrogenation of Ketones," *Mini-Reviews in Organic Chemistry*, 2008, 5, 313-322.

* cited by examiner

*Primary Examiner* — Michael Barker
(74) *Attorney, Agent, or Firm* — Foley & Lardner LLP

(57) ABSTRACT

Novel polymeric rhodium catalysts having repeating subunits of Formula (I), wherein $R^1$-$R^8$, X, A, m, n and p are as defined in the application, are described along with methods of using these catalysts, as well as precursors therefor, in the chemical synthesis transformations.

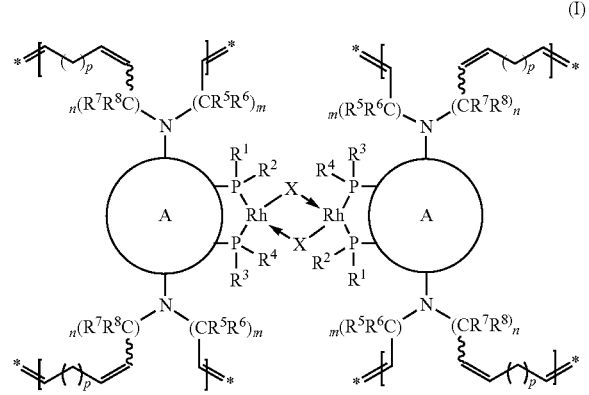

38 Claims, No Drawings

HETEROGENEOUS RHODIUM METAL CATALYSTS

RELATED APPLICATIONS

This application is a U.S. National Stage of PCT International Application No. PCT/CA2010/001547, filed Sep. 28, 2010, which claims the benefit of U.S. Provisional Application No. 61/246,166, filed Sep. 28, 2009. The foregoing applications are hereby incorporated herein by reference in their entireties.

FIELD

The present application is in the field of heterogeneous rhodium metal catalysts, and their use in chemical syntheses, in particular the asymmetric chemical syntheses.

BACKGROUND

Asymmetric catalysis is an important field of chemistry, with high activity in academic laboratories and with many applications in the agrochemical,[1] flavoring,[2] fragrance,[2] and pharmaceutical[3] industries. For example, 75% of small-molecule drugs approved in 2006 by the United States Food and Drug Administration were of a single enantiomer.[4] Often, one enantiomer of a chiral pharmaceutical has desirable bioactivity, while its opposite is less active or toxic. For example, Naproxen is a widely-used anti-inflammatory drug. The (S)-enantiomer is 30 times more effective than the (R)-enantiomer.[5] Thus a lower dose of the (S)-enantiomer is sufficient for the desired effect, thereby reducing toxic side effects. This difference in activity between enantiomers in biological systems is the major driving force behind academic and industrial research in asymmetric synthesis. The common, general methods to prepare enantiomerically enriched chemicals include resolution of racemates, transformation of naturally available chiral compounds, chirality transfer reactions, and asymmetric catalysis.[6] Of these, asymmetric catalysis is among the most efficient methods to amplify source chirality. In addition, catalysis reduces the waste and byproducts associated with large-scale chemical production.

Common challenges in asymmetric catalysis are that the catalysts are costly and air sensitive. Further, typical asymmetric catalysts contain toxic metals and ligands that must be removed from the products in order to comply with health and safety standards for industry, in particular pharmaceuticals.[7,8] The most direct method to reduce both catalyst cost and product contamination is to develop reusable catalysts that are easily removed from the product mixture by filtration or by use of a flow reactor.

Towards these ends, a great deal of research has been carried out to develop immobilized homogenous catalysts that can be isolated by simple filtration and reused. A wide variety of approaches are documented and the interested reader is directed towards the following reviews: chiral-modified surfaces,[9] encapsulation,[10] electrostatic interactions,[11] biphasic or ionic liquid systems,[12] and covalent tethering.[13,14] Of these methods, the least intrusive to the integrity of the active site is the covalent attachment of the chiral ligand in the catalyst to a solid support.[15] The alternative, anchoring through the metal, has a large effect on the coordination environment around the active site. The methods used to covalently immobilize homogeneous catalysts include radical co-polymerization of vinyl arenes and vinyl substituted ligands,[16-19] condensation of alcohols or amines with acid derivatives,[20-24] coupling reactions,[25,26] and polymerizations between amines and isocyanates.[27,28]

An immobilized homogeneous ruthenium catalyst for hydrogenation reactions was recently assembled using a metal-containing monomer in a ring-opening metathesis polymerization (ROMP) reaction that was effected using an alternating polymerization reaction between a ruthenium-containing monomer and the spacer monomer cyclooctene (COE).[29,30] In more recent work, this hydrogenation methodology was extended to the use of BINAP (BINAP=2,2'-bis (diphenylphosphino)-1,1'-binaphthyl) via the preparation of (R)-5,5'-dinorimido BINAP.[30]

The intramolecular cycloisomerization of enynes is catalyzed by a variety of transition metals including ruthenium,[31] palladium,[32] platinum,[32,33] nickel,[34] iridium,[35,36] gold [33,37] and rhodium.[38] The asymmetric, rhodium-catalyzed cycloisomerization of 1,6-enynes was first reported by the Zhang group in 2000.[39] The literature catalyst is best generated in situ by reacting [(COD)RhCl]$_2$ (COD=1,5-cyclooctadiene) with BINAP (1 equivalent per Rh atom) in 1,2-dichloroethylene, and then adding AgSbF$_6$ (2 equivalents per Cl).[40] This reaction has been used to prepare a variety of products, including tetrahydrofurans,[40] lactams,[41] lactones,[42] cyclopentanes,[43] and cyclopentanones.[43] As far as the inventors are aware, there are no examples in the literature where this catalyst has been successfully immobilized for heterogeneous-type reactions. The homogeneous examples require impractically high loadings of "[Rh(BINAP)]$^+$", usually 10 mol %, along with 20 mol % of AgSbF$_6$ as activator. The high cost and toxicity of Rh, BINAP, and AgSbF$_6$ prevent the commercial application of this reaction.[44]

SUMMARY

A novel, reusable, high turn-over polymer based catalyst framework has been developed. This catalyst is particularly useful for the asymmetric cycloisomerization of enynes. Specifically, the 5,5-dinorimido BINAP ligand was used to prepare a rhodium based catalyst that was co-polymerized with cyclooctene using alternating ring-opening metathesis polymerization (ROMP) to produce an immobilized catalyst system. Uniquely, the catalyst comprised chloride bridges that crosslinked the active site resulting in a three-dimensional framework. This crosslinking creates a more compact framework that is opened by removal of the chlorides, for example by treatment with silver salts. The resulting immobilized catalyst was able to effect the intramolecular cycloisomerization of enyne substrates, for example producing a total of more than 600 turnovers over seven runs with most runs occurring with over 91% yield.

Accordingly the present application includes a polymeric catalyst comprising repeating subunits of the formula I:

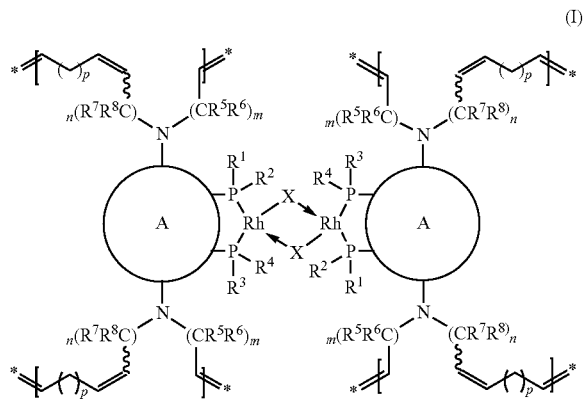

(I)

wherein
$R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl and halo;

(A) is a binaphthyl group or a derivative of a binaphthyl group, each being unsubstituted or substituted with one or more groups independently selected from $C_{1-6}$alkyl, $OC_{1-6}$alkyl and halo;

$R^5$, $R^6$, $R^7$ and $R^8$ are independently selected from H, $C_{1-6}$alkyl, $OC_{1-6}$alkyl and halo,
or
$R^5$ and $R^6$ and/or $R^7$ and $R^8$ are =O,
or
one of $R^5$ and $R^6$ is linked to one of $R^7$ and $R^8$ to form, together with the atoms to which they are attached and the atoms connecting them, a monocyclic, bicyclic or tricylic ring system,
$R^5$, $R^6$, $R^7$ and $R^8$ in each methylene unit is the same or different,
and $\sim$ means the double bond attached to this bond is in the cis or trans configuration, if applicable;
m and n are, independently, an integer between and including 0 and 10;
p is an integer between and including 1 and 14; and
X is an anionic ligand.

The present application also includes compounds of formula II, useful as precursors to the polymers of formula I as well as catalysts for metal-catalyzed organic synthesis reactions,

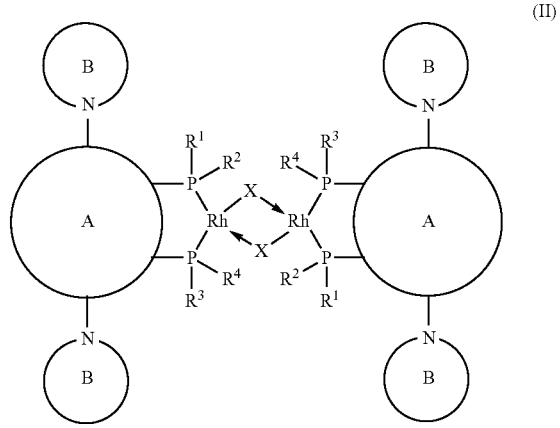

(II)

wherein $R^1$, $R^2$, $R^3$, $R^4$, X and (A) are as defined in formula I above; and (B) is a monocyclic, bicyclic or tricylic group comprising at least one double bond and being unsubstituted or substituted with one or more groups independently selected from $C_{1-6}$alkyl, $OC_{1-6}$alkyl, halo and =O.

The present application also includes a method of performing metal-catalyzed organic synthesis reactions comprising contacting substrates for the organic synthesis reaction with a catalyst comprising repeating subunits of the formula I as defined above and/or a catalyst comprising a compound of formula II as defined above under conditions for performing the organic synthesis reaction, and optionally isolating one or more products from the organic synthesis reaction. In an embodiment of the application, the organic synthesis reaction is any reaction that benefits from the presence or use of a metal catalyst, for example, but not limited to, cycloisomerizations, hydrosilations, hydrogenations, conjugate additions and cross-couplings. In an embodiment of the application, the organic synthesis transformation is an asymmetric or chiral synthesis reaction (i.e. provides one enantiomer in excess of the other).

In an embodiment of the application, the organic synthesis reaction is an intramolecular cycloisomerization reaction, accordingly, there is also included, a method for the intramolecular cycloisomerization of enynes comprising contacting one or more compounds having at least one enyne grouping with a catalyst comprising repeating subunits of the formula I as defined above and/or a catalyst comprising a compound of formula II as defined above in the presence of an anion abstracting agent under conditions suitable for the intramolecular cycloisomerization of the at least one enyne grouping.

In another embodiment, the organic synthesis reactions are performed in a flow through reactor, with or without a solvent.

Other features and advantages of the present application will become apparent from the following detailed description. It should be understood, however, that the detailed description and the specific examples while indicating preferred embodiments of the application are given by way of illustration only, since various changes and modifications within the scope of the application will become apparent to those skilled in the art from this detailed description.

DETAILED DESCRIPTION i. Definitions

The term "$C_{1-q}$alkyl" as used herein means straight and/or branched chain, saturated alkyl radicals containing from one to "q" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable q is an integer representing the largest number of carbon atoms in the alkyl radical.

The term "$C_{4-8}$cycloalkyl" as used herein means a monocyclic, saturated carbocylic group containing from four to eight carbon atoms and includes cyclobutyl, cyclopentyl, cyclohexyl, cyclopentyl and cyclooctyl.

The term "halo" as used herein means chloro, bromo, iodo or fluoro.

The term "monocyclic, bicyclic or tricylic ring system" as used herein refers a carbon-containing ring system, that includes monocycles, fused and spirocyclic bicyclic and tricyclic rings and bridged rings. Where specified, the carbons in the rings may be substituted or replaced with heteroatoms.

The term "linked to" as used herein means that the referenced groups are joined via a linker group which is a direct bond or an alkylene chain which, where specified, the carbons in the chain may be substituted or replaced with heteroatoms.

The compounds of formulae I, II and III have at least one asymmetric centre. Where these compounds possess more than one asymmetric centre, they may exist as diastereomers. It is to be understood that all such isomers and mixtures thereof in any proportion are encompassed within the scope of the present application. It is to be understood that while the stereochemistry of the compounds of the present application may be as shown for any given compound listed herein, such compounds may also contain certain amounts (for example less than 30%, less than 20%, less than 10%, or less than 5%) of the corresponding compounds having alternate stereochemistry.

The term "suitable", as in for example, "suitable anionic ligand" or "suitable reaction conditions" means that the selection of the particular group or conditions would depend on the specific synthetic manipulation to be performed and the identity of the molecule but the selection would be well within the skill of a person trained in the art. All process steps described herein are to be conducted under conditions suitable to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In some cases the chemistries outlined herein may have to be modified, for instance by use of protecting groups, to prevent side reactions of reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not destroy or decompose the molecule. Many conventional protecting groups are known in the art, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999. These may include but are not limited to Boc, Ts, Ms, TBDMS, TBDPS, Tf, Bn, allyl, Fmoc, $C_{1-16}$acyl, silyl, and the like.

The term "intramolecular cycloisomerization" as used here refers to a reaction wherein two or more functional groups in the same molecule react with each other to form a cyclic structure with the isomerization of one or more double or triple bonds.

The term "isomerization" as used herein refers to the process by which one molecule is transformed into another molecule which has exactly the same atoms, but the atoms are rearranged.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The definitions and embodiments described in particular sections are intended to be applicable to other embodiments herein described for which they are suitable as would be understood by a person skilled in the art.

ii. Compounds

The present application includes novel polymeric catalysts comprising repeating subunits of the formula I:

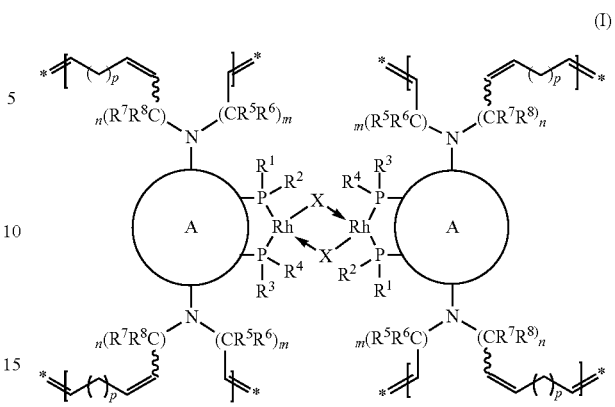

wherein $R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl and halo;

(A) is a binaphthyl group or a derivative of a binaphthyl group, each being unsubstituted or substituted with one or more groups independently selected from $C_{1-6}$alkyl, $OC_{1-6}$alkyl and halo;

$R^5$, $R^6$, $R^7$ and $R^8$ are independently selected from H, $C_{1-6}$aklkyl $OC_{1-6}$alkyl and halo, or $R^5$ and $R^6$ and/or $R^7$ and $R^8$ are =O, or one of $R^5$ and $R^6$ is linked to one of $R^7$ and $R^8$ to form, together with the atoms to which they are attached and the atoms connecting them, a monocyclic, bicyclic or tricylic ring system, $R^5$, $R^6$, $R^7$ and $R^8$ in each methylene unit is the same or different, and ∿ means the double bond attached to this bond is in the cis or trans configuration, if applicable;

m and n are, independently, an integer between and including 0 and 10;

p is an integer between and including 1 and 14; and

X is an anionic ligand.

In an embodiment of the application, $R^1$, $R^2$, $R^3$ and $R^4$ independently are selected from phenyl and cyclohexyl, the latter two groups being unsubstituted or substituted with 1, 2, 3, 4, or 5 groups independently selected from $C_{1-4}$alkyl, $OC_{1-4}$alkyl, chloro and fluoro. In a further embodiment of the application $R^1$, $R^2$, $R^3$ and $R^4$ independently are selected from phenyl and cyclohexyl, the latter two groups being unsubstituted or substituted with 1, 2, 3, 4, or 5 groups independently selected from $CH_3$, $OCH_3$, chloro and fluoro. In a further embodiment of the application, $R^1$, $R^2$, $R^3$ and $R^4$ are the same. In a further embodiment, $R^1$, $R^2$, $R^3$ and $R^4$ are each phenyl that is unsubstituted or substituted with 1, 2, 3, 4, or 5 groups independently selected from $C_{1-4}$alkyl, $OC_{1-4}$alkyl, chloro and fluoro. In another embodiment, $R^1$, $R^2$, $R^3$ and $R^4$ are each unsubstituted phenyl.

In another embodiment of the application, $R^5$, $R^6$, $R^7$ and $R^8$ are independently selected from H, $OC_{1-4}$alkyl, $OC_{1-4}$alkyl and halo, or $R^5$ and $R^6$ and/or $R^7$ and $R^8$ are =O, or one of $R^5$ and $R^6$ is linked to one of $R^7$ and $R^8$ to form, together with the atoms to which they are attached and the atoms connecting them, a monocyclic or bicyclic ring system, and $R^5$, $R^6$, $R^7$ and $R^8$ in each methylene unit is the same or different.

In another embodiment, $R^5$, $R^6$, $R^7$ and $R^8$, m and n, together with the atoms to which they are attached and the atoms connecting them, form a group selected from:

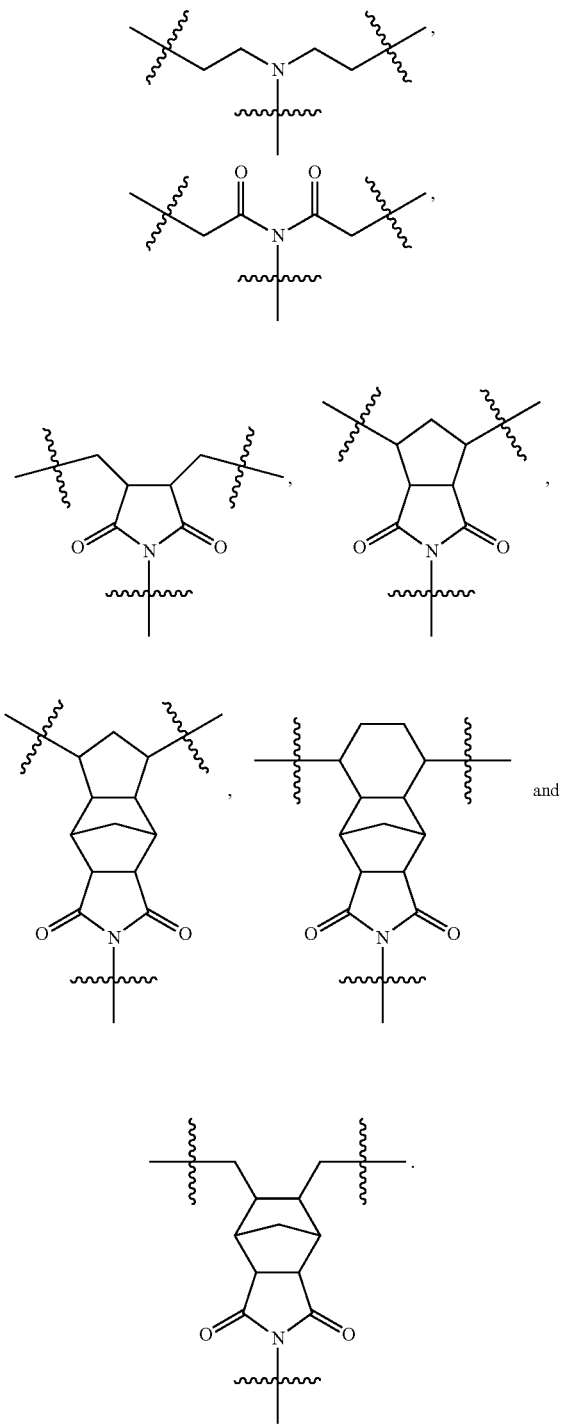

and

In another embodiment, $R^5$, $R^6$, $R^7$ and $R^8$, m and n, together with the atoms to which they are attached and the atoms connecting them, form

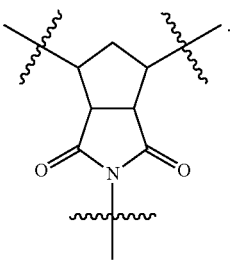 [SMILES: *C1CC(*)C2C(=O)N(*)C(=O)C12]

In another embodiment of the present application, (A) is a binaphthyl group or a derivative of a binaphthyl group, each being unsubstituted or substituted with 1, 2, 3, 4, 5 or 6 groups independently selected from $C_{1-4}$alkyl, $OC_{1-4}$alkyl, chloro and fluoro. In another embodiment, (A) is 1,1'-binaphthyl, 5,5',6,6',7,7',8,8'-octahydro-1,1'-binaphthyl or 12,13,14,15,16,17,12',13',14',15',16',17'-dodecahydro-11H,11'H-[4,4']bi[cyclopenta[a]phenanthrenyl] each being unsubstituted or substituted with 1, 2, 3, 4, 5 or 6 groups independently selected from $C_{1-4}$alkyl, $OC_{1-4}$alkyl, chloro and fluoro. In a particular embodiment of the present application (A) is optically active and the compounds of formula I comprise a substantially pure optical isomer of (A).

Ligands having the structure,

are known in the art and are commonly abbreviated as BINAP and various derivatives thereof. Some of the known derivatives of BINAP that are within the scope of the present application include, but are not limited to each optical isomer of 2,2'-bis-(diphenylphosphino)-1,1'-binaphthyl (abbreviated name: BINAP); BINAP derivatives in which the naphthalene ring of BINAP is partially reduced, such as each optical isomer of 2,2'-bis(diphenylphosphino)-5,5',6,6',7,7',8,8'-octahydro-1,1'-binaphthyl (abbreviated name: $H_8$BINAP); BINAP derivatives in which the naphthalene ring of BINAP carries substituent(s), such as each optical isomer of 2,2'-bis-(diphenylphosphino)-6,6'-dimethyl-1,1'-binaphthyl (abbreviated name: 6MeBINAP); BINAP derivatives in which the benzene ring on the phosphorus atom of BINAP is substituted with lower alkyl group(s), such as each optical isomer of 2,2'-bis-(di-p-tolylphosphino)-1-,1'-binaphthyl (abbreviated name: Tol-BINAP), each optical isomer of 2,2'-bis[bis(3-methylphenyl)phosphino]-1,1'-binaphthyl, each optical isomer of 2,2'-bis[bis(3,5-di-tert-butylphenyl)phosphino]-1,1'-binaphthyl, each optical isomer of 2,2'-bis[bis(4-tert-butylphenyl)phosphino]-1,1'-binaphthyl, each optical isomer of 2,2'-bis[bis(3,5-dimethylphenyl)phosphino]-1,1'-binaphthyl (abbreviated name: Xyl-BINAP), and each optical isomer of 2,2'-bis[bis(3,5-dimethyl-4-methoxyphenyl)phosphino]-1,1'-binaphthyl (abbreviated name: Dmanyl-BINAP); BINAP derivatives in which the naphthalene ring of BINAP carries substituent(s) and the benzene ring on the phosphorus atom of BINAP is substituted with from 1 to 5 $C_{1-6}$alkyl substituents, such as each optical isomer of 2,2'-bis[bis-(3,5- dimethylphenyl)phosphino]-6,6'-dimethyl-1,1'-binaphthyl (abbreviated name: Xyl-6MeBINAP), and, BINAP derivatives in which the naphthalene ring of BINAP is condensed with a saturated hydrocarbon ring, such as each optical isomer of 3,3'-bis-(diphenylphosphanyl)-13,13'-dimethyl-12, 13,14,15,16,17,12',13',14',15',16',17'-dodecahydro-11H, 11'H-[4,4]bi[cyclopenta[a]phenanthrenyl].

It is an embodiment of the present application that the polymeric catalyst comprises repeating subunits of formula I shown below:

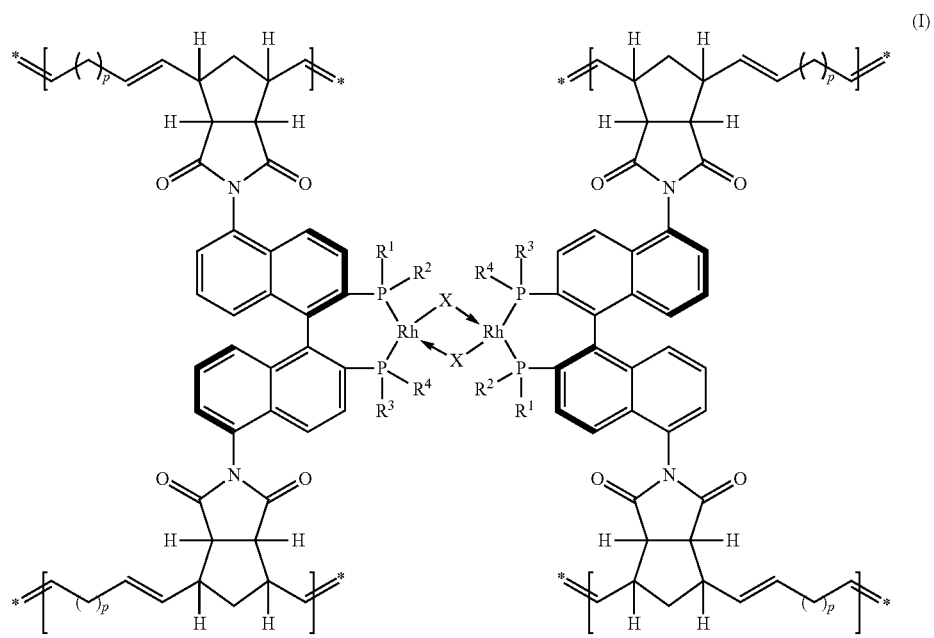

(I)

wherein
$R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl and halo; and
p is an integer between and including 1 and 14; and
X is an anionic ligand,
or an alternate optical isomer thereof.

In an embodiment of the present application, p is 2, 3, 4, 5, 6, 7, 8 or 9. In a further embodiment, p is 5, 6, 7, 8 or 9.

In an embodiment of the present application, X is a halide, suitably chloride.

In an another embodiment of the application, the repeating subunit of formula I has the following relative stereochemistry:

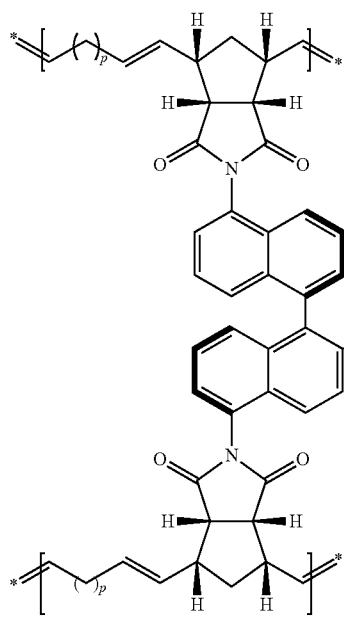
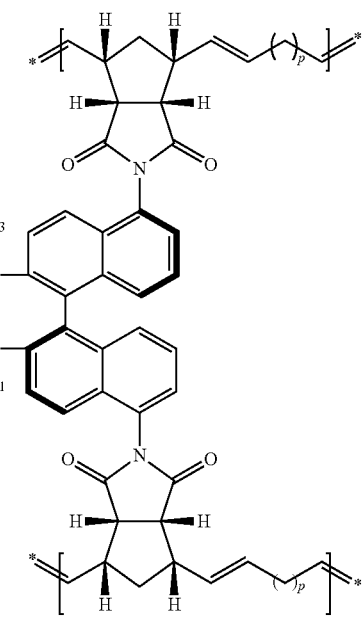

wherein

R¹, R², R³ and R⁴ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl and halo; and p is an integer between and including 1 and 14; and X is an anionic ligand, or an alternate optical isomer thereof.

In an embodiment of the present application the catalysts comprising repeating subunits of the formula I are prepared using alternating ROMP assembly of a cycloolefin and a catalyst precursor the formula II, wherein (A), X, R¹, R², R³ and R⁴ are as defined in formula I, prepared, for example by reacting a compound of the formula III, wherein (A), R¹, R², R³ and R⁴ are as defined in formula I and (B) is a monocyclic, bicyclic or tricylic group comprising at least one double bond and being unsubstituted or substituted with one or more groups independently selected from $C_{1-6}$alkyl, $OC_{1-6}$alkyl, halo and =O, with, for example, a reagent of the formula IV, wherein X is as defined in formula I and L is any suitable displaceable ligand such as $C_2H_4$, in a suitable organic solvent, such as methylene chloride, at a temperature of about 20° C. to about 40° C., suitably about 30° C., for about 10 minutes to about 12 hours, suitably about 1 hour (see Scheme 1). Compounds of formula III are prepared, for example, using procedures described previously in the art.[30]

Scheme 1

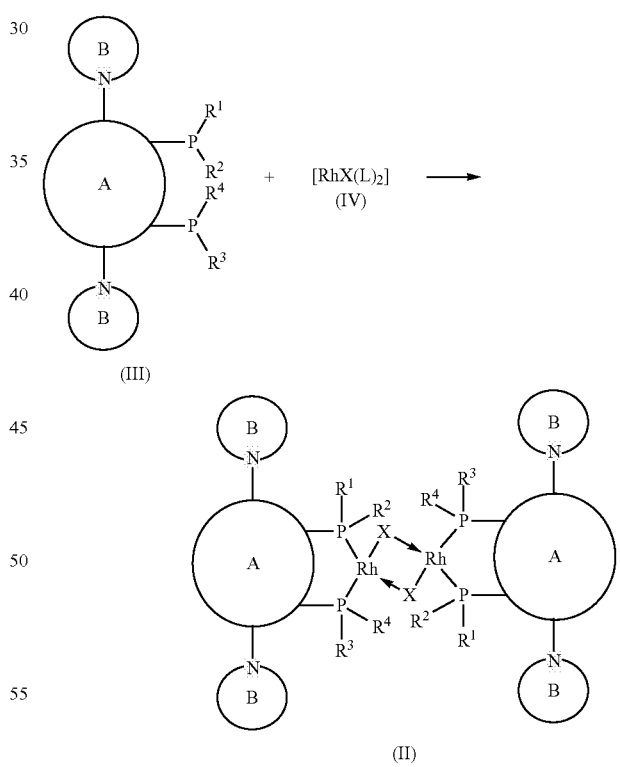

In an embodiment of the application, the alternating ROMP assembly of the precursor of formula II, wherein (A), X, R¹, R², R³ and R⁴ are as defined in formula I and (B) is a monocyclic, bicyclic or tricylic group comprising at least one double bond and being unsubstituted or substituted with one or more groups independently selected from $C_{1-6}$alkyl, $OC_{1-6}$alkyl, halo and =O, is carried out in a suitable organic solvent, for example methylene chloride at a temperature or about 20° C. to about 60° C., suitably about 40° C. using a cycloolefin, such as cyclooctene, as spacer and a ROMP catalyst, such as a Grubbs catalyst (for example $RuCl_2(PCy_3)_2CHPh$), a Schrock catalyst or any other metathesis catalyst (for example those described in Bielawski, C. W. and Grubbs R. H. *Prog. Polym. Sci.* 2007, 32:1-29), for about 1 hour to about 48 hours, suitably about 28 hours. In an embodiment, the mole ratio of the compound of formula II:cycloolefin:catalyst is about 10:120:1.

The alternating ROMP assembly of compounds of formula II and cycloolefin produces a three-dimensional catalyst organic framework that is different from the Ru framework synthesized previously for the ketone hydrogenations.[30] Specifically, the anionic ligand bridges in I are expected to crosslink the active sites of the resulting framework. This crosslinking creates a more compact framework that will be opened by removal of the anionic ligands, for example by reaction with silver salts. The resulting opened framework will still hold the Rh centres in pairs, with each Rh centre in proximity to the other. This proximity could lead to bimetallic cooperativity, and, more importantly, it provides a built-in method to protect the active sites of the catalyst between runs. A challenge that is common to the reuse of solid catalysts in batch-type reactions is that the catalyst must be protected between the runs, when the product mixture is filtered off the catalyst, and fresh reactant mixture is reintroduced. In general, catalysts that have the desired high activity for a given reaction, are also unstable on their own, and do not survive the filtration and recharge steps. In solution, complexes of the formula

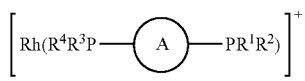

are known to dimerize by forming $\eta^6$-aryl bonds to the Rh centres.[45] These $\eta^6$-aryl bonds stabilize the Rh centre in the absence of substrate, and will stabilize the [Rh(BINAP)]$^+$ centres in the framework between runs. The $\eta^6$-aryl bonds are expected to break in the presence of substrate or a coordinating solvent to regenerate the catalyst.

The present application also includes compounds of formula II, useful as precursors to the polymers of formula I,

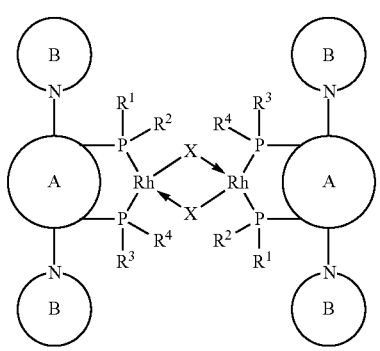

(II)

wherein $R^1$, $R^2$, $R^3$, $R^4$, X and Ⓐ are as defined in formula I above and ⒷN is a monocyclic, bicyclic or tricylic group comprising at least one double bond and being unsubstituted or substituted with one or more groups independently selected from $C_{1-6}$alkyl, $OC_{1-6}$alkyl, halo and =O.

In embodiment of the application, ⒷN is selected from:

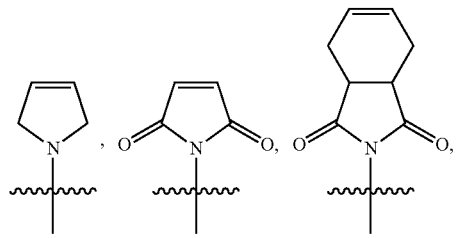

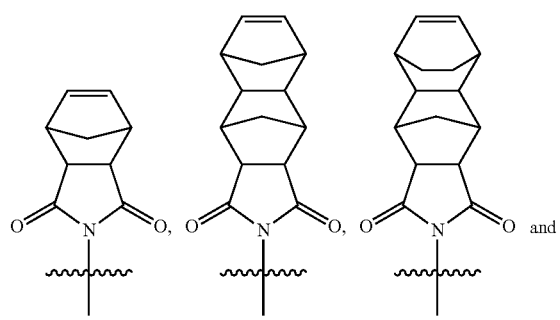

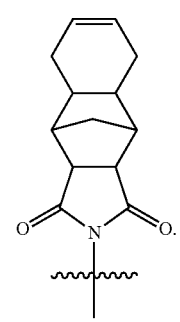

In a further embodiment, ⒷN is

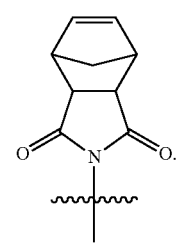

In another embodiment of the present application, when 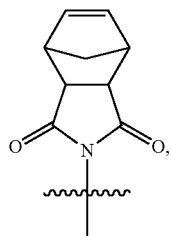 [SMILES: *N1C(=O)C2C3C=CC(C3)C2C1=O] is the compounds of formula II have the following relative stereochemistry:

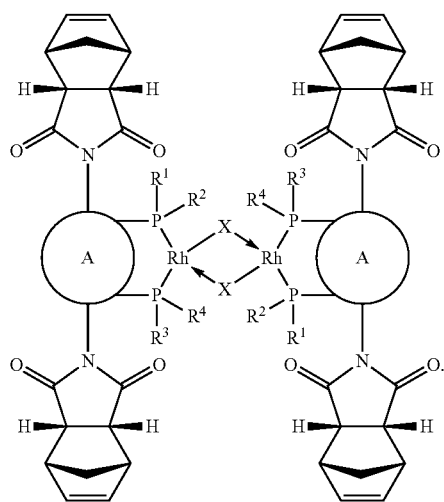

(II)

The compounds of formula II are also useful as catalysts for metal-catalyzed organic synthesis reactions as described in greater detail hereinbelow.

iii. Methods

The present application also includes a method of performing metal-catalyzed organic synthesis reactions comprising contacting substrates for the organic synthesis reaction with a catalyst comprising repeating subunits of the formula I as defined above and/or a catalyst comprising a compound of formula II as defined above under conditions for performing the organic synthesis reaction, and optionally isolating one or more products from the organic synthesis reaction. In an embodiment of the application, the organic synthesis reaction is any reaction that benefits from the presence or use of a metal catalyst, for example, but not limited to, cycloisomerizations, hydrosilations, hydrogenations, conjugate additions and cross-couplings. In an embodiment of the application, the organic synthesis transformation is an asymmetric or chiral synthesis reaction (i.e. provides one enantiomer in excess of the other).

In an embodiment of the application, the organic synthesis reaction is an intramolecular cycloisomerization reaction, accordingly, there is also included, a method for the intramolecular cycloisomerization of enynes comprising contacting one or more compounds having at least one enyne grouping with a catalyst comprising repeating subunits of the formula I as defined above and/or a catalyst comprising a compound of formula II as defined above in the presence of an anion abstracting agent under conditions suitable for the intramolecular cycloisomerization of the at least one enyne grouping.

The compounds having at least one enyne grouping are suitably any compound comprising at least one double bond ("ene") and at least one triple bond ("yne"), the double bond and triple bond being arranged spatially so that they are able to undergo an intramolecular cycloisomerization reaction. The compounds optionally also comprise one or more other functional groupings including for example, ethers, amides, carbonyls, thioethers, amines, sulfoxides, sulfones, silanes, siloxanes and any combination thereof, as long as the functional grouping does not impede the cycloisomerization reaction. A person skilled in the art would be able to readily identify enyne compounds suitable for use in the method of the present application. Examples of such compounds are found, for example, in Michelet, V.; Toullec, P.Y.; Genet, J.-P. Angew. Chem. Int. Ed. 2008, 47:4268-4315. In an embodiment of the application, the enyne is a 1,6-enyne or a 1,7-enyne, suitably a 1,6-enyne.

In an embodiment the catalyst framework is deposited as a thin film on to a substrate, for example, but not limited to $BaSO_4$, barium (L)- and (D)-tartrates, aluminum oxide ($Al_2O_3$), silica ($SiO_2$), $Fe_3O_4$, Teflon™, Celite™, AgCl and sand to prevent agglomeration of the catalyst and to provide mechanical stability toward long-term stirring.

In a further embodiment the anion abstracting agent is a silver salt, such as but not limited to, $AgSbF_6$, $AgPF_6$, $AgBF_4$, $AgClO_4$, AgBARF (BARF=tetrakis(3,5-bis(trifluoromethyl)-phenyl)-borate), AgOTf (OTf=trifluoromethanesulfonate–$CF_3SO_3^-$) or any other silver salt with a weakly-coordinating counterion. In a further embodiment the anion abstracting agent is a thallium salt, such as but not limited to, $TlPF_6$. In an embodiment, the amount of anion abstracting agent used is about 1 mol % to about 10 mol %. Note that the anion abstracting agent is only used in the first run and need not be re-added upon addition of further compounds having at least one enyne grouping.

In a further embodiment, the conditions for the intramolecular cycloisomerization of the at least one enyne grouping include the use of a suitable solvent. In an embodiment the solvent is 1,4-dioxane, methanol, tetrahydrofuran, 2-methyltetrahydrofuran, cyclopentylmethylether, 1,2-dimethoxyethane, dichloroethane, dichloromethane, acetone or ethanol or a mixture thereof. In an embodiment the solvent is 2-methyltetrahydrofuran.

In another embodiment, the conditions for the intramolecular cycloisomerization of the at least one enyne grouping include using a mole ratio of substrate:catalyst of about 10:1 to about 1,000,000:1, 10:1 to about 100,000:1, 10:1 to about 10,000:1, 10:1 to about 5000:1, about 20:1 to about 2500:1, or about 25:1 to about 1000:1.

In another embodiment, the conditions for the intramolecular cycloisomerization of the at least one enyne grouping include a temperature of about 0° C. to about 120° C., 30° C. to about 100° C., suitably about 40° C. to about 90° C., for 1 hour to about 96 hours.

In another embodiment, the method of performing metal catalyzed organic synthesis reactions using the catalysts comprising repeating subunits of formula I as defined above and/or a catalyst comprising a compound of formula II as defined above, is performed in a flow through-type reactor. In this embodiment, the catalyst is comprised in a flow-through reactor, such as a column, and substrates and any other required reactants, with or without a solvent, are injected into the input end of the reactor. The reaction takes place inside the reactor, as the substrate and reactants flow through the reactor, contacting the catalyst, and the products are isolated from the output end of the reactor. Flow through the reactor may be facilitated by gravity or using gas pressure. Flow through reactors and methods for their use are well-known in the art (for a recent review article on asymmetric catalysis in flow reactors, see "Asymmetric Reactions in Continuous Flow", by Xiao Yin Mak, Paola Laurino, and Peter H Seeberger: Beilstein J. Org. Chem. 2009; volume 5, 19). For catalysts of formula II, attachment to or absorption on to a solid support is desirable for flow-through reactors. Methods of attaching or absorbing catalysts to solid supports are known in the art.

The present application also includes a composition comprising a compound of formula I, a compound of formula II, or a mixture thereof and an anion abstracting anion. In an embodiment the anion abstracting agent is a silver salt, such as but not limited to, $AgSbF_6$, $AgPF_6$, $AgBF_4$, $AgClO_4$, AgBARF (BARF=tetrakis(3,5-bis(trifluoromethyl)-phenyl)-borate), AgOTf (OTf=trifluoromethanesulfonate–$CF_3SO_3^-$) or any other silver salt with a weakly-coordinating counterion. The composition may be formulated or packaged as a kit for sale of the compounds of formula I and/or II as catalysts for metal-catalyzed organic synthesis reactions. Therefore the present application also includes a kit comprising a compound of formula I, a compound of formula II or a mixture thereof and an anion abstracting agent, either in one composition or in separate compositions, optionally, with instructions for use.

The following non-limiting examples are illustrative of the present application:

EXAMPLES

Example 1

Preparation of Catalyst Precursor IIa

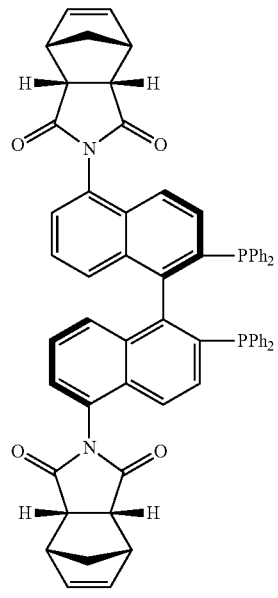

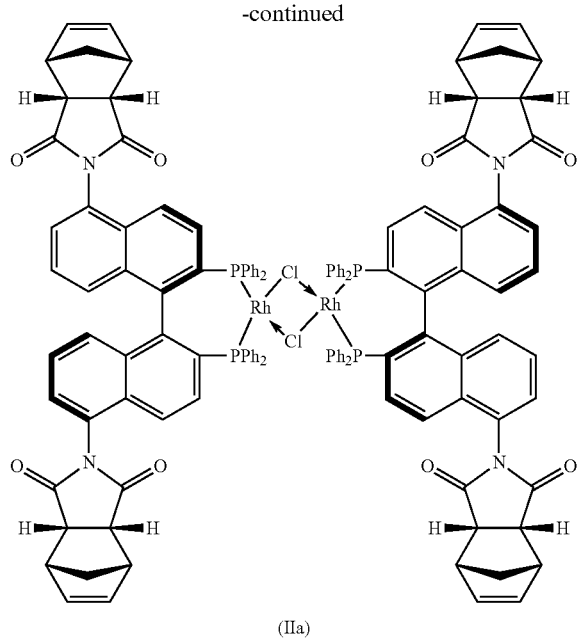

The catalyst precursor, [RhCl((R)—N-BINAP)]$_2$ (IIa), was synthesized by reacting (R)-5,5'-dinorimido-BINAP (IIIa) with μ-dichlorotetraethylene dirhodium(I) (IVa) in $CH_2Cl_2$. The reaction solutions of IIa were used directly, without isolation of IIa, for the ROMP assembly.

Example 2

ROMP Assembly of Catalyst Precursor IIa and COE

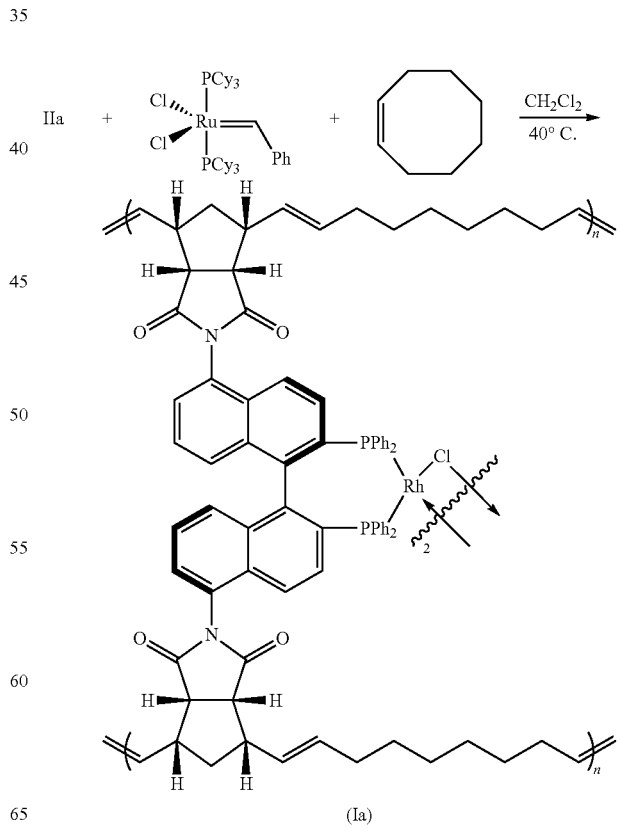

The alternating ROMP assembly of IIa was carried out in CH$_2$Cl$_2$ at 40° C. using cyclooctene (COE) as spacer and RuCl$_2$(PCy$_3$)$_2$(CHPh) as the catalyst in a 20:120:1 mole ratio. $^1$H and $^{31}$P NMR spectroscopy showed that the COE and IIa were consumed after 28 h.

Example 3

Intramolecular cyclization of (3-((Z)-pent-2-enyloxy)prop-1-ynyl)cyclohexane (1)

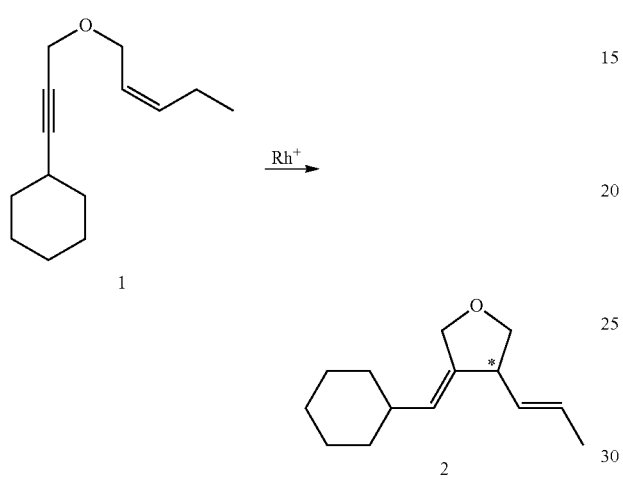

This cyclization was set up using 5 mol % Rh. Specifically, 20 equiv of 1 were added to a suspension of the BaSO$_4$-supported rhodium-organic framework Ia in dioxane, the mixture was vigorously stirred for 1 min, and 2 equiv of AgSbF$_6$ were added suspended in dioxane. The cyclization was complete after 3 h of vigorous stirring at 60° C. All the literature reports of Rh-catalyzed asymmetric cyclizations of enynes use 10 mol % Rh catalyst (10 turnovers) except for one unconfirmed report using ~1 mol % catalyst and a reactive substrate. Thus this example provides the highest number of turnovers that has been obtained for the direct asymmetric cyclization of an unreactive enyne using a chiral Rh-diphosphine catalyst. Somewhat higher turnovers, using ~3 mol % catalyst have been reported in the literature when the product is intercepted or trapped using reagents such as boronic acids, silanes, or hydrogen. Such indirect cyclizations are atom inefficient, however, and they place restrictions on the types of substrates and products that can be used or obtained. Further, this is the first time 1 has been successfully cyclized via such a reaction. Attempts to perform the reaction using the literature catalyst system, [((R)-BINAP)RhCl]$_2$ and AgSbF$_6$ gave complicated mixtures of products. Thus, for this substrate at least, the catalyst-organic framework is a more effective cyclization catalyst than the homogenous system.

Surprisingly, it was found that the same catalyst (compound Ia) could be used for a total of seven runs without adding further silver (I) hexafluoroantimonate. Table 1 summarizes the results that were obtained with this system. There was a drop in activity by run 4, but this drop was compensated for by heating the reaction. Temperatures up to 65° C. were used for runs 4 through 7 with no observable difference in the product obtained. Thus, the same catalyst produced a total of 720 turnovers over seven runs, with most runs occurring with over 91% yield. Nevertheless, the present catalyst system is a step-increase in activity over the 10 turnovers currently reported as the state of the art in the open literature. Experiments were repeated using higher loadings of the substrate:catalyst (e.g. 500:1 to 1000:1) and the results are presented in Table 2.

Example 4

Intramolecular cyclication of 1-(3-((Z)-pent-2-enyloxy)prop-1-ynyl)benzene (3)

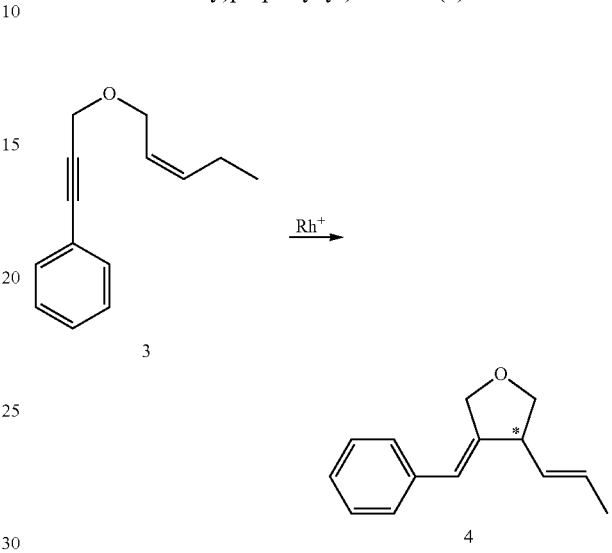

The catalyst organic framework of the present application was also surprisingly active for the cyclization of the phenyl substrate 3. The results are summarized in Tables 3 and 4. The first run was performed at the same temperature (60° C.) as the first run of Example 3. The temperature was then reduced to 50° C. for runs 2-4. The reaction with 3 was slower than with 1, likely because of competitive η$^6$-aryl binding of the substrate or product to the Rh centre of the catalyst. Higher temperatures were therefore required for the cyclization of 3. The ee for the reaction was greater than 99.9%, as the peak of the minor product was not detectable within rejection limits of the GC (0.025% of major peak integration). There again was a drop in activity after run 3 that was compensated by increasing the temperature. It is noted that increasing the temperature did not decrease the ee of the reaction. Conversions for each run ranged between 76% and 100%, with the total number of turnovers being 380 turnovers over 5 runs which appears to be the highest number of turnovers for any enantioselective rhodium catalyst in the cyclization of enynes.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Recycling of catalyst framework Ia for the cyclization of 1.[a]

| Run | Temp. (° C.) | Time (h) | Conversion (%)[c] |
|---|---|---|---|
| 1[b] | 60 | 3 | >99 |
| 2 | 50[d] | 18 | >99 |
| 3 | 50 | 22.5 | >99 |
| 4[d] | 50 | 22 | ~99 |
|  | 65[e] | 4 | >99 |
| 5 | 65 | 19.5 | >99 |
| 6 | 65 | 24 | >99 |
| 7 | 65 | 24 | >99 |

[a]The reaction was carried out in 0.2M solution of 1 in 1,4-dioxane under the following conditions: Sub./Rh. = 100/1; except for run 1.
[b]Sub./AgSbF$_6$/Rh = 20/2/1.
[c]Conversion determined by $^1$H NMR analysis.
[d]Temperature was decreased to 50° C. after initial run done at 60° C. for 3 hours.
[e]Run was not complete after 22 hours at 50° C., so the temperature was increased to 65° C. and reaction was run until completion, which occurred after an additional four hours at 65° C.

TABLE 2

High-loading cyclizations of 1 using catalyst framework Ia.

| Loading (Sub:Rh:AgSbF$_6$) | Temperature (° C.) | Solvent | Time (h) | Conversion (%) | TON |
|---|---|---|---|---|---|
| 1000:1:5 | 70 | 1,4-dioxanes | 45 | 80.0 | 800 |
| 1000:1:5 | 70 | 2MeTHF | 4 | 63.0 | 630 |
| 500:1:5 | 70 | 2MeTHF | 2 | 100 | 500 |

1000:1 loadings were carried out in 2M 1 in the solvent mentioned in the table and the 500:1 loadings were carried out in 1M 1 in the solvent mentioned in the table. This was to maintain the amount of solvent covering the catalyst as a constant. For all reactions, the supported catalyst framework Ia was weighed into a schlenk tube, along with solid AgSbF$_6$. The substrate was then added under inert atmosphere, and rinsed in with the appropriate amount of solvent. Reaction flasks were then placed in the temperature controlled bath for the amount of time specified.

TABLE 3

Recycling of catalyst framework Ia for cyclization of 3.[a]

| Run | Temp. (° C.) | Time (h) | Eq[b] | Conversion (%)[c] | ee (%)[c] |
|---|---|---|---|---|---|
| 1[d] | 60 | 3 | 20 | 100 | >99.9 |
| 2[e] | 50 | 18.5 | 100 | 18 | >99.9 |
|  | 70 | 23.5 | 100 | 96 | >99.9 |
| 3 | 70 | 48 | 100 | 91 | >99.9 |
| 4 | 80 | 69.5 | 100 | 97 | >99.9 |
| 5 | 92 | 117 | 100 | 76 | >99.9 |

[a]The reaction was carried out in 0.2M solution of 3 in 1,4-dioxane except for run 1.
[b]No. Eq of substrate vs. catalyst.
[c]Conversion and ee were determined by chiral GC analysis.
[d]0.1M solution of 3 was used.
[e]Temperature raised to 70° C. after 18.5 hours and allowed to go to completion for an additional 23.5 hours.

TABLE 4

High-loading cyclizations of 3 using catalyst framework Ia.

| Loading (Sub:Rh:AgSbF$_6$) | Temperature (° C.) | Time (h) | Conversion (%) | TON | ee (%) |
|---|---|---|---|---|---|
| 300:1:5[a] | 70 | 19.75 | 100 | 300 | >99.9 |
| 200:1[b,c] | 70 | 17 | 91 | 182 | >99.9 |

[a]The reaction was carried out in 0.6M solution of 3 in dioxanes.
[b]The reaction was carried out with 0.4M solution of 3 in dioxanes.
[c]Used same catalyst as previous with minimal rinsing with dioxanes, AgSbF$_6$ addition was not necessary. Total TON for the catalyst is 482.

FULL CITATIONS FOR DOCUMENTS REFERRED TO IN THE SPECIFICATION (1) Ramos Tombo, G. M.; Bellus, D. "Chirality and crop protection" *Angewandte Chemie (International Edition in English)* 1991, 30, 1193-1215.
(2) Saudan, L. A. "Hydrogenation Processes in the Synthesis of Perfumery Ingredients" *Acc. Chem. Res.* 2007, 40, 1309-1319.
(3) Klingler, F. D. "Asymmetric Hydrogenation of Prochiral Amino Ketones to Amino Alcohols for Pharmaceutical Use" *Acc. Chem. Res.* 2007, 40, 1367-1376.
(4) Thayer, A. M. "Centering on chirality" *Chemical and Engineering News* 2007, 85, 11-19.
(5) Koul, S.; Parshad, R.; Taneja, S.C.; Qazi, G. N. "Enzymatic resolution of naproxen" *Tetrahedron: Asymmetry* 2003, 14, 2459-2465.
(6) Noyori, R. In *Asymmetric Catalysis in Organic Synthesis*; Wiley: New York, 1994, pp 378.
(7) Garrett, C. E.; Prasad, K. "The art of meeting palladium specifications in active pharmaceutical ingredients produced by Pd-catalyzed reactions" *Advanced Synthesis and Catalysis* 2004, 346, 889-900.
(8) MacQuarrie, S.; Horton, J. H.; Barnes, J.; McEleney, K.; Loock, H.-.; Crudden, C. M. "Visual observation of redistribution and dissolution of palladium during the Suzuki-Miyaura reaction" *Angewandte Chemie—International Edition* 2008, 47, 3279-3282.
(9) Studer, M.; Blaser, H.; Exner, C. "Enantioselective Hydrogenation Using Heterogeneous Modified Catalysts: An Update" *Advanced Synthesis and Catalysis* 2003, 345, 45-65.
(10) Li, C. "Chiral synthesis on catalysts immobilized in microporous and mesoporous materials" *Catalysis Reviews—Science and Engineering* 2004, 46, 419-492.
(11) Cheng, H.; Hao, J.; Wang, H.; Xi, C.; Meng, X.; Cai, S.; Zhao, F. "(R,R)-DPEN-modified Ru/γ-Al2O3—An efficient heterogeneous catalyst for enantioselective hydrogenation of acetophenone" *Journal of Molecular Catalysis A: Chemical* 2007, 278, 6-11.
(12) Ooi, T.; Maruoka, K. "Recent advances in asymmetric phase-transfer catalysis" *Angewandte Chemie—International Edition* 2007, 46, 4222-4266.
(13) Heitbaum, M.; Glorius, F.; Escher, I. "Asymmetric heterogeneous catalysis" *Angewandte Chemie—International Edition* 2006, 45, 4732-4762.
(14) McMorn, P.; Hutchings, G. J. "Heterogeneous enantioselective catalysts: Strategies for the immobilisation of homogeneous catalysts" *Chemical Society Reviews* 2004, 33, 108-122.
(15) Tóth, I.; van Geem, Paul C. In *Immobilization Techniques*; de Vries, Johannes G., Elsevier, C. J., Eds.; The Handbook of Homogeneous Hydrogenation; Wiley-VCH: Weinheim, 2007; Vol. 3, pp 1421-1467.

(16) Kim, J.-.; Lee, D.-.; Jun, B.-.; Lee, Y.-. "Copper-free Sonogashira cross-coupling reaction catalyzed by polymer-supported N-heterocyclic carbene palladium complex" *Tetrahedron Letters* 2007, 48, 7079-7084.

(17) Kim, J.; Kim, J.; Shokouhimehr, M.; Lee, Y. "Polymer-Supported N-Heterocyclic Carbene-Palladium Complex for Heterogeneous Suzuki Cross-Coupling Reaction" *J. Org. Chem.* 2005, 70, 6714-6720.

(18) Bianchini, C.; Barbaro, P.; Dal Santo, V.; Gobetto, R.; Meli, A.; Oberhauser, W.; Psaro, R.; Vizza, F. "Immobilization of Optically Active Rhodium-Diphosphine Complexes on Porous Silica via Hydrogen Bonding" *Advanced Synthesis and Catalysis* 2001, 343, 41-45.

(19) Bianchini, C.; Frediani, M.; Mantovani, G.; Vizza, F. "Synthesis of polymer-supported rhodium(I)-1,3-bis(diphenylphosphino)propane moieties and their use in the heterogeneous hydrogenation of quinoline and benzylideneacetone" *Organometallics* 2001, 20, 2660-2662.

(20) Nakai, Y.; Kimura, T.; Uozumi, Y. "Alkylative Cyclization of 1,6-Enynes in Water with an Amphiphilic Resin-Supported Palladium Catalyst" *Synlett* 2006, 18, 3065-3068.

(21) Nakai, Y.; Uozumi, Y. "Cycloisomerization of 1,6-Enynes: Asymmetric Multistep Preparation of a Hydrindane Framework in Water with Polymeric Catalaysts" *Org. Lett.* 2005, 7, 291-293.

(22) Nakai, Y.; Uozumi, Y. "An Amphiphilic Resin-Supported Palladium Catalyst for High-Throughput Cross-Coupling in Water" *Org. Lett.* 2002, 4, 2997-3000.

(23) Uozumi, Y.; Nakazono, M. "Amphiphilic Resin-Supported Rhodium-Phosphine Catalysts for C—C Bond Forming Reactions in Water" *Adv. Synth. Catal.* 2002, 344, 274-277.

(24) Uozumi, Y.; Kimura, T. "Heck Reaction in Water with Amphiphilic Resin-Supported Palladium-Phosphine Complexes" *Synlett* 2002, 2045-2048.

(25) Yu, H.-.; Hu, Q.-.; Pu, L. "The first optically active BINOL-BINAP copolymer catalyst: Highly stereoselective tandem asymmetric reactions [?]" *Journal of the American Chemical Society* 2000, 122, 6500-6501.

(26) Yu, H.-.; Hu, Q.-.; Pu, L. "Synthesis of a rigid and optically active poly(BINAP) and its application in asymmetric catalysis" *Tetrahedron Letters* 2000, 41, 1681-1685.

(27) Saluzzo, C.; Lamouille, T.; Hérault, D.; Lemaire, M. "Polymer-supported catalysts: Enantioselective hydrogenation and hydrogen transfer reduction" *Bioorganic and Medicinal Chemistry Letters* 2002, 12, 1841-1844.

(28) Saluzzo, C.; Lamouille, T.; Le Guyader, F.; Lemaire, M. "Synthesis and studies of 6,6'-BINAP derivatives for the heterogeneous asymmetric hydrogenation of methyl acetoacetate" *Tetrahedron Asymmetry* 2002, 13, 1141-1146.

(29) Ralph, C. K.; Akotsi, O. M.; Bergens, S. H. "A Reusable Polymeric Asymmetric Hydrogenation Catalyst Made by Ring-Opening Olefin Metathesis Polymerization" *Organometallics* 2004, 23, 1484-1486.

(30) Ralph, C. K.; Bergens, S. H. "A Highly Reusable Catalyst for Enantioselective Ketone Hydrogenation. Catalyst-Organic Frameworks by Alternating ROMP Assembly" *Organometallics* 2007, 26, 1571-1574.

(31) Trost, B. M.; Toste, F. D. "Ruthenium-Catalyzed Cycloisomerizations of 1,6- and 1,7-Enynes" *J. Am. Chem. Soc.* 2000, 122, 714-715.

(32) Michelet, V.; Charruault, L.; Gladiali, S.; Genet, J.-. "Alkoxy- and hydroxycyclization of enynes catalyzed by Pd(II) and Pt(II) catalysts" *Pure and Applied Chemistry* 2006, 78, 397-407.

(33) Zhang, L.; Sun, J.; Kozmin, S. A. "Gold and platinum catalysis of enyne cycloisomerization" *Advanced Synthesis and Catalysis* 2006, 348, 2271-2296.

(34) Tekavec, T. N.; Louie, J. "Nickel-catalyzed cycloisomerization of enynes: catalyst generation via C—H activation of carbene ligands" *Tetrahedron* 2008, 64, 6870-6875.

(35) Chatani, N.; Inoue, H.; Morimoto, T.; Muto, T.; Murai, S. "Iridium (I)-catalyzed cycloisomerization of enynes" *Journal of Organic Chemistry* 2001, 66, 4433-4436.

(36) Kezuka, S.; Okado, T.; Niou, E.; Takeuchi, R. "Iridium complex-catalyzed reaction of 1,6-enynes: Cycloaddition and cycloisomerization" *Organic Letters* 2005, 7, 1711-1714.

(37) Nieto-Oberhuber, C.; Muñoz, M. P.; López, S.; Jiménez-Núñez, E.; Nevado, C.; Herrero-Gómez, E.; Raducan, M.; Echavarren, A. M. "Gold(I)-catalyzed cyclizations of 1,6-enynes: Alkoxycyclizations and exol endo skeletal rearrangements" *Chemistry—A European Journal* 2006, 12, 1677-1693.

(38) Zhang, Z.; Zhu, G.; Tong, X.; Wang, F.; Xie, X.; Wang, J.; Jiang, L. "Transition metal-catalyzed intramolecular enyne cyclization reaction" *Current Organic Chemistry* 2006, 10, 1457-1478.

(39) Cao, P.; Zhang, X. "The First Highly Enantioselective Rh-Catalyzed Enyne Cycloisomerization" *Angew. Chem. Int. Ed.* 2000, 39, 4104-4106.

(40) Lei, A.; He, M.; Wu, S.; Zhang, X. "Highly Enantioselective Rh-Catalyzed Intramolecular Alder-Ene Reactions for the Syntheses of Chiral Tetrahydrofurans" *Angew. Chem. Int. Ed.* 2002, 114, 3607-3610.

(41) Lei, A.; Waldkirch, J. P.; He, M.; Zhang, X. "Highly Enantioselective Cycloisomerization of Enynes Catalyzed by Rhodium for the Preparation of Functionalized Lactams" *Angew. Chem. Int. Ed.* 2002, 41, 4526-4529.

(42) He, M.; Lei, A.; Zhang, X. "Enantioselective syntheses of 3,4,5-trisubstituted γ-lactones: Formal synthesis of (−)-blastmycinolactol" *Tetrahedron Letters* 2005, 46, 1823-1826.

(43) Liu, F.; Liu, Q.; He, M.; Zhang, X.; Lei, A. "Rh-catalyzed highly enantioselective formation of functionalized cyclopentanes and cyclopentanones" *Org. Biomol. Chem.* 2007, 5, 3531-3534.

(44) Hashmi, A. Stephen K.; Haufe, P.; Nass, A. R. "On the Enantioselective Rhodium-Catalyzed Enyne Cyclization" *Adv. Synth. Catal.* 2003, 345, 1237-1241.

(45) Miyashita, A.; Yasuda, A.; Takaya, H.; Toriumi, K.; Ito, T.; Souchi, T.; Noyori, R. "Synthesis of 2,2'-bis(diphenylphosphino)-1,1'-binaphthyl (BINAP), an atropisomeric chiral bis(triaryl)phosphine, and its use in the rhodium(I)-catalyzed asymmetric hydrogenation of α-(acylamino) acrylic acids" *J. Am. Chem. Soc.* 1980, 102, 7932-7934.

The invention claimed is:
1. A polymeric catalyst comprising repeating subunits of the formula I:

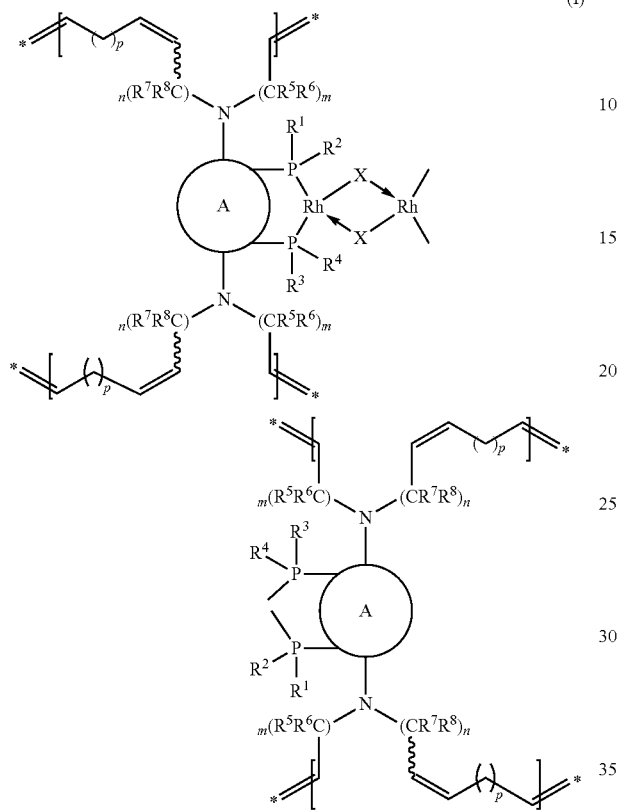

wherein
$R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$ alkyl and halo;

Ⓐ is a binaphthyl group or a derivative of a binaphthyl group, each being unsubstituted or substituted with one or more groups independently selected from $C_{1-6}$alkyl, $OC_{1-6}$alkyl and halo;
$R^5$, $R^6$, $R^7$ and $R^8$ are independently selected from H, $C_{1-6}$alkyl, $OC_{1-6}$alkyl and halo; or
$R^5$ and $R^6$ and/or $R^7$ and $R^8$ are =O; or
one of $R^5$ and $R^6$ is linked to one of $R^7$ and $R^8$ to form, together with the atoms to which they are attached and the atoms connecting them, a monocyclic, bicyclic or tricylic ring system;
$R^5$, $R^6$, $R^7$ and $R^8$ in each methylene unit is the same or different, and ⌇ means the double bond attached to this bond is in the cis or trans configuration, if applicable;
m and n are, independently, an integer between and including 0 and 10;
p is an integer between and including 1 and 14; and
X is an anionic ligand.

2. The catalyst of claim 1, wherein $R^1$, $R^2$, $R^3$ and $R^4$ independently are selected from phenyl and cyclohexyl, the latter two groups being unsubstituted or substituted with 1, 2, 3, 4, or 5 groups independently selected from $C_{1-4}$alkyl, $OC_{1-4}$ alkyl, chloro and fluoro.

3. The catalyst of claim 2, wherein $R^1$, $R^2$, $R^3$ and $R^4$ independently are selected from phenyl and cyclohexyl, the latter two groups being unsubstituted or substituted with 1, 2, 3, 4, or 5 groups independently selected from $CH_3$, $OCH_3$, chloro and fluoro.

4. The catalyst of claim 1, wherein $R^1$, $R^2$, $R^3$ and $R^4$ are the same.

5. The catalyst of claim 4, wherein $R^1$, $R^2$, $R^3$ and $R^4$ are each phenyl that is unsubstituted or substituted with 1, 2, 3, 4, or 5 groups independently selected from $C_{1-4}$alkyl, $OC_{1-4}$ alkyl, chloro and fluoro.

6. The catalyst of claim 5, wherein $R^1$, $R^2$, $R^3$ and $R^4$ are each unsubstituted phenyl.

7. The catalyst of claim 1, wherein Ⓐ is a binaphthyl group or a derivative of a binaphthyl group, each being unsubstituted or substituted with 1, 2, 3, 4, 5 or 6 groups independently selected from $C_{1-4}$alkyl, $OC_{1-4}$alkyl, chloro and fluoro.

8. The catalyst of claim 7, wherein Ⓐ is 1,1'-binaphthyl, 5,5',6,6', 7,7',8,8'-octahydro-1,1'-binaphthyl or 12,13,14,15,16,17,12',13',14',15',16',17'-dodecahydro-11H,11'H-[4,4']bi[cyclopenta[a]phenanthrenyl] each being unsubstituted or substituted with 1, 2, 3, 4, 5 or 6 groups independently selected from $C_{1-4}$alkyl, $OC_{1-4}$alkyl, chloro and fluoro.

9. The catalyst of claim 1, wherein Ⓐ is optically active and the compounds of formula 1 comprise a substantially pure optical isomer of Ⓐ.

10. The catalyst of claim 1 wherein

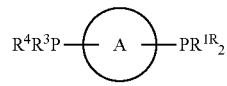

is selected from each optical isomer of
(a) 2,2'-bis-(diphenylphosphino)-1,1'-binaphthyl (abbreviated name: BINAP);
(b) BINAP derivatives in which the naphthalene ring of BINAP is partially reduced;
(c) BINAP derivatives in which the naphthalene ring of BINAP carries substituent(s);
(d) BINAP derivatives in which the benzene ring on the phosphorus atom of BINAP is substituted with lower alkyl group(s);
(e) BINAP derivatives in which the naphthalene ring of BINAP carries substituent(s) and the benzene ring on the phosphorus atom of BINAP is substituted with from 1 to 5 $C_{1-6}$alkyl substituents; and
(f) BINAP derivatives in which the naphthalene ring of BINAP is condensed with a saturated hydrocarbon ring.

11. The catalyst of claim 10 selected from each optical isomer of 2,2'-bis-(diphenylphosphino)-1,1'-binaphthyl (abbreviated name: BINAP), each optical isomer of 2,2'-bis (diphenylphosphino)-5,5',6,6',7,7',8,8'-octahydro-1,1'-binaphthyl (abbreviated name: $H_8$BINAP), each optical isomer of 2,2'-bis-(diphenylphosphino)-6,6'-dimethyl-1,1'-binaphthyl (abbreviated name: 6MeBINAP), each optical isomer of 2,2'-bis-(di-p-tolylphosphino)-1-,1'-binaphthyl (abbreviated name: Tol-BINAP), each optical isomer of 2,2'-bis[bis(3-methylphenyl)phosphino]-1,1'-binaphthyl, each optical isomer of 2,2'-bis[bis(3,5-di-tert-butylphenyl)phosphino]-1,1'-binaphthyl, each optical isomer of 2,2'-bis[bis(4-tert-butylphenyl)phosphino]-1,1'-binaphthyl, each optical isomer of 2,2'-bis[bis(3,5-dimethylphenyl)phosphino]-1,1'-binaphthyl (abbreviated name: Xyl-BINAP), each optical isomer of 2,2'-bis[bis(3,5-dimethyl-4-methoxyphenyl)phosphino]-1,1'-binaphthyl (abbreviated name: Dmanyl-BINAP), each optical isomer of 2,2'-bis[bis-(3,5- dimethylphenyl)phosphino]-6,6'-dimethyl-1,1'-binaphthyl (abbreviated name: Xyl-6MeBINAP), and each optical isomer of 3,3'-bis-(diphenylphosphanyl)-1313'-dimethyl-12,13,14,15,16,17,12',13', 14',15',16',17'-dodecahydro-11H,11'H-[4,4]bi[cyclopenta[a]phenanthrenyl].

12. The catalyst of claim 11, wherein (A) is an optical isomer of 1,1-binaphthyl.

13. The catalyst of claim 1, wherein $R^5$, $R^6$, $R^7$ and $R^8$ are independently selected from H, $C_{1-4}$alkyl, $OC_{1-4}$alkyl, and halo, or $R^5$ and $R^6$ and/or $R^7$ and $R^8$ are =O, or one of $R^5$ and $R^6$ is linked to one of $R^7$ and $R^8$ to form, together with the atoms to which they are attached and the atoms connecting them, a monocyclic or bicyclic ring system, and $R^5$, $R^6$, $R^7$ and $R^8$ in each methylene unit is the same or different.

14. The catalyst of claim 13, wherein $R^5$, $R^6$, $R^7$ and $R^8$, m and n, together with the atoms to which they are attached and the atoms connecting them, form a group selected from:

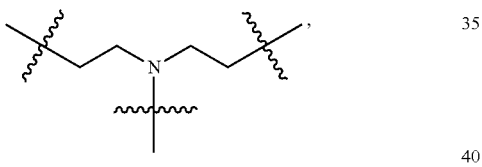

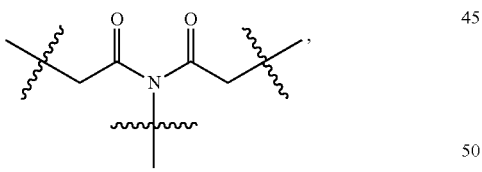

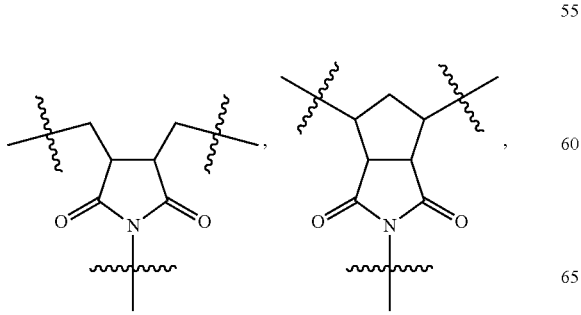

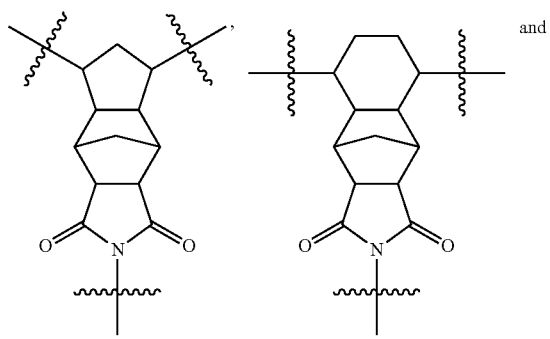

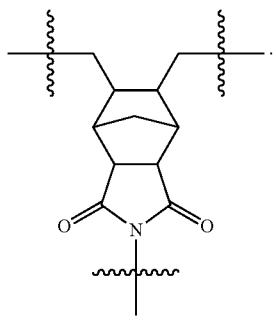

15. The catalyst of claim 14, wherein $R^5$, $R^6$, $R^7$ and $R^8$, m and n, together with the atoms to which they are attached and the atoms connecting them, form

I

16. The catalyst of claim 1, comprising repeating subunits of formula I:

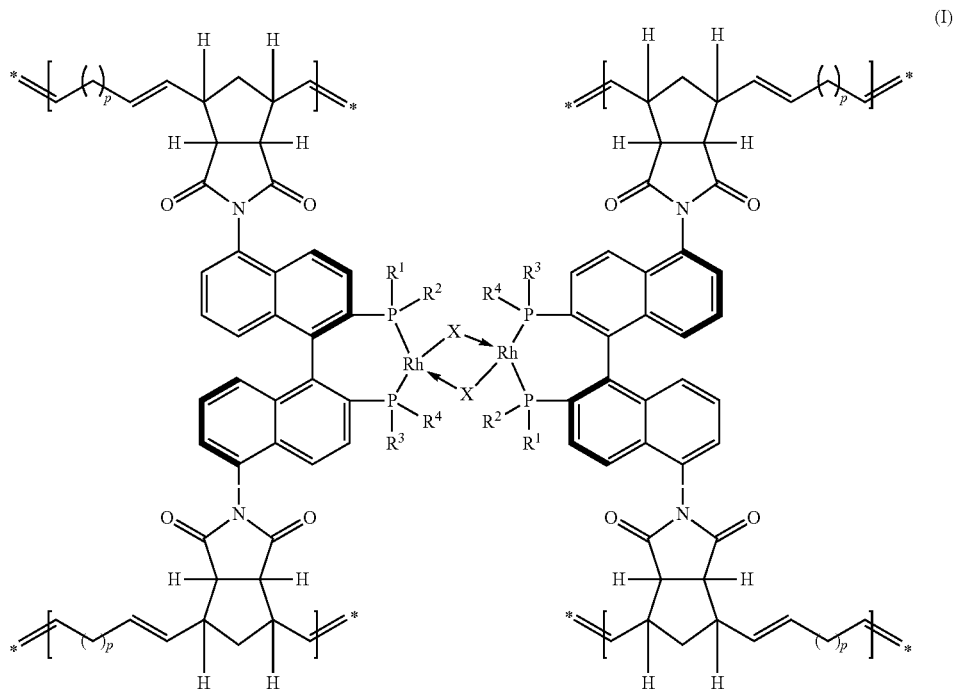

wherein
$R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl, and halo;

p is an integer between and including 1 and 14; and

X is an anionic ligand;

or an alternate optical isomer thereof.

17. The catalyst of claim 16, wherein the repeating subunit of formula I has the following relative stereochemistry:

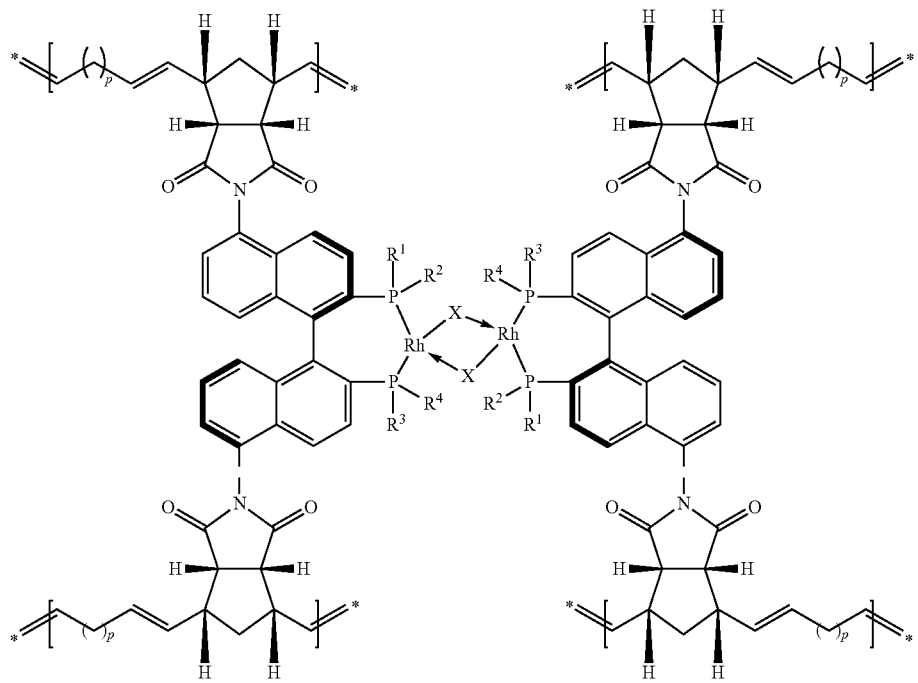

wherein

R$^1$, R$^2$, R$^3$ and R$^4$ are independently selected from phenyl and C$_{4-8}$cycloalkyi, the latter two groups being unsubstituted or substituted, where possible, with 1, 2, 3, 4, or 5 groups independently selected from C$_{1-6}$alkyl, OC$_{1-6}$alkyl and halo;

p is an integer between and including 1 and 14; and

X is an anionic ligand;

or an alternate optical isomer thereof.

18. The catalyst of claim 1, wherein X is a halide.

19. A compound of formula II:

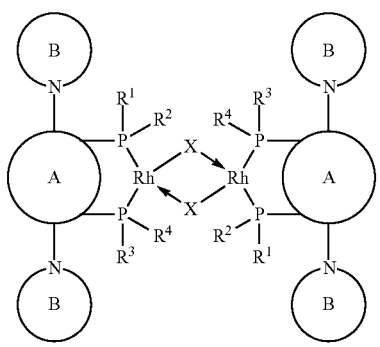

(II)

wherein

R$^1$, R$^2$, R$^3$ and R$^4$ are independently selected from phenyl and C$_{4-8}$cycloalkyl, the latter two groups being unsubstituted or substituted, where possible, with 1, 2, 3, 4, or 5 groups independently selected from C$_{1-6}$alkyl, OC$_{1-6}$alkyl and halo;

(A) is a binaphthyl group or a derivative of a binaphthyl group, each being unsubstituted or substituted with one or more groups independently selected from C$_{1-6}$alkyl, OC$_{1-6}$alkyl and halo;

X is an anionic ligand; and (B/N) is a monocyclic, bicyclic or tricylic group comprising at least one double bond and being unsubstituted or substituted with one or more groups independently selected from C$_{1-6}$alkyl, OC$_{1-6}$alkyl, halo and =O.

20. The compound of claim 19, wherein (B/N) is selected from:

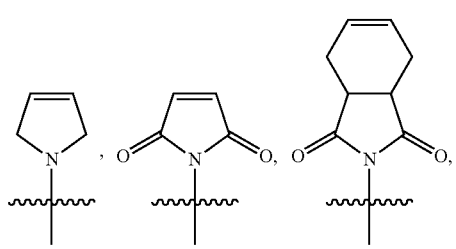

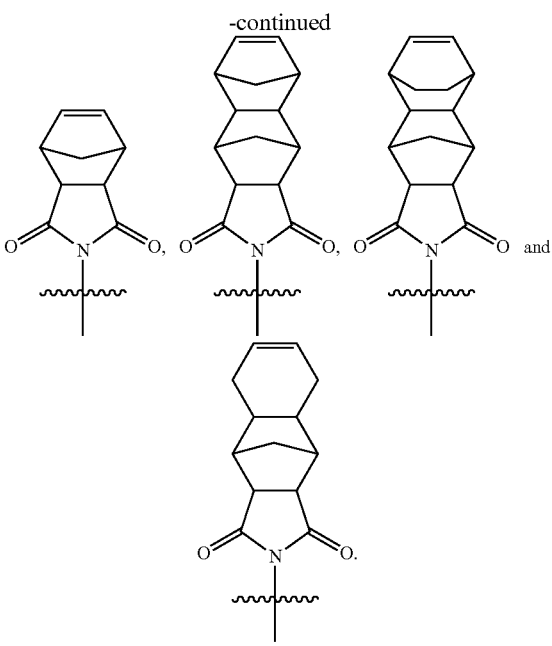

21. The compound of claim 20, wherein (B/N) is

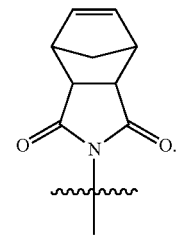 [SMILES: *N1C(=O)C2C3C=CC(C3)C2C1=O]

22. The compound of claim 21, having the following relative stereochemistry:

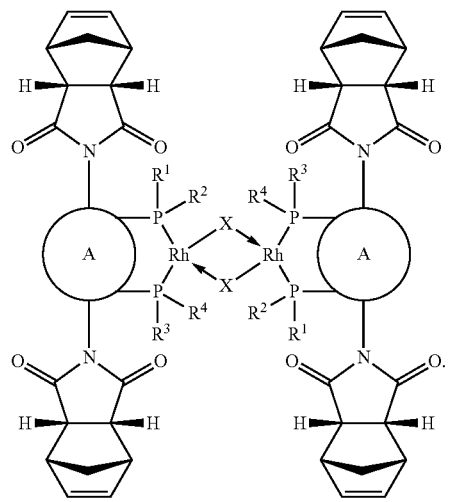

(II)

23. A method of performing metal-catalyzed organic synthesis reactions comprising contacting substrates for the organic synthesis reaction with a catalyst comprising repeating subunits of the formula I, a catalyst comprising a compound of formula II, or a combination thereof, under conditions for performing the organic synthesis reaction, and optionally isolating one or more products from the organic synthesis reaction;

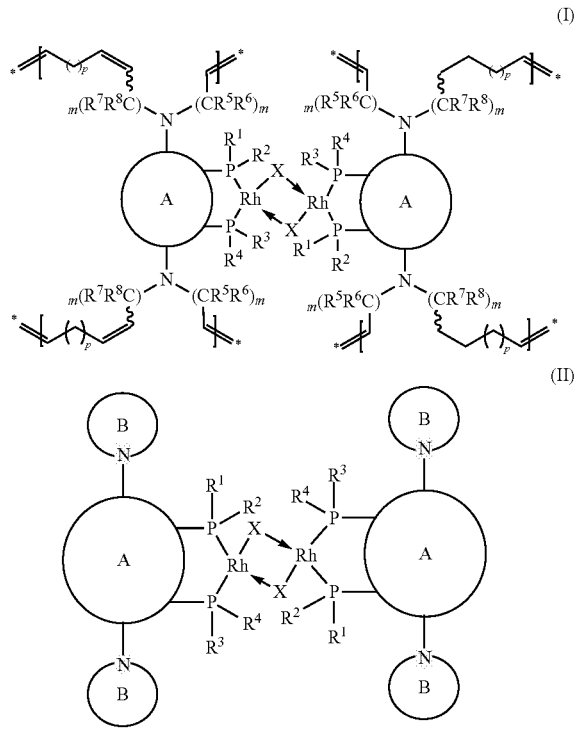

wherein
$R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$ alkyl and halo;

(A) is a binaphthyl group or a derivative of a binaphthyl group, each being unsubstituted or substituted with one or more groups independently selected from $C_{1-6}$alkyl, $OC_{1-6}$alkyl and halo;

(B/N) is a monocyclic, bicyclic or tricylic group comprising at least one double bond and being unsubstituted or substituted with one or more groups independently selected from $C_{1-6}$alkyl, $OC_{1-6}$alkyl, halo and =O;
$R^5$, $R^6$, $R^7$ and $R^8$ are independently selected from H, $C_{1-6}$alkyl, $OC_{1-6}$alkyl and halo; or
$R^5$ and $R^6$ and/or $R^7$ and $R^8$ are =O; or
one of $R^5$ and $R^6$ is linked to one of $R^7$ and $R^8$ to form, together with the atoms to which they are attached and the atoms connecting them, a monocyclic, bicyclic or tricylic ring system;
$R^5$, $R^6$, $R^7$ and $R^8$ in each methylene unit is the same or different, and ⌇ means the double bond attached to this bond is in the cis or trans configuration, if applicable;
m and n are, independently, an integer between and including 0 and 10;

p is an integer between and including 1 and 14; and
X is an anionic ligand.

24. The method of claim 23, wherein the organic synthesis reaction is selected from cycloisomerizations, hydrosilations, hydrogenations, conjugate additions and cross-couplings.

25. The method of claim 23 wherein the organic synthesis reaction is an asymmetric or chiral synthesis reaction.

26. A method for the intramolecular cycloisomerization of enynes comprising contacting one or more compounds having at least one enyne grouping with a catalyst comprising repeating subunits of the formula I, a catalyst comprising a compound of formula II, or a combination thereof, in the presence of an anion abstracting agent under conditions suitable for the intramolecular cycloisomerization of the at least one enyne grouping;

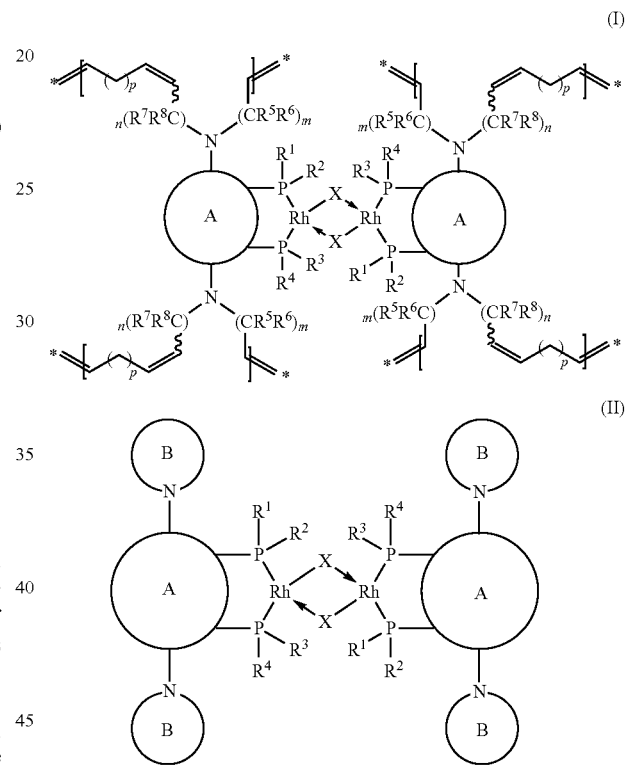

wherein
$R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$ alkyl and halo;

(A) is a binaphthyl group or a derivative of a binaphthyl group, each being unsubstituted or substituted with one or more groups independently selected from $C_{1-6}$alkyl, $OC_{1-6}$alkyl and halo;

(B/N) is a monocyclic, bicyclic or tricylic group comprising at least one double bond and being unsubstituted or substituted with one or more groups independently selected from $C_{1-6}$alkyl, $OC_{1-6}$alkyl, halo and =O;
$R^5$, $R^6$, $R^7$ and $R^8$ are independently selected from H, $C_{1-6}$alkyl, $OC_{1-6}$alkyl and halo; or $R^5$ and $R^6$ and/or $R^7$ and $R^8$ are =O; or one of $R^5$ and $R^6$ is linked to one of $R^7$ and $R^8$ to form, together with the atoms to which they are attached and the atoms connecting them, a monocyclic, bicyclic or tricylic ring system;

$R^5$, $R^6$, $R^7$ and $R^8$ in each methylene unit is the same or different, and ∿ means the double bond attached to this bond is in the cis or trans configuration, if applicable;

m and n are, independently, an integer between and including 0 and 10;

p is an integer between and including 1 and 14; and

X is an anionic ligand.

27. The method of claim 26, wherein the catalyst is deposited as a thin film on to a substrate.

28. The method of claim 27, wherein the substrate is $BaSO_4$.

29. The method of claim 26, wherein the anion abstracting agent is a silver salt.

30. The method of claim 29, wherein the silver salt is $AgSbF_6$.

31. The method of claim 26, wherein the amount of anion abstracting agent used is about 1 mol % to about 10 mol %.

32. The method of claim 26, wherein the conditions for the intramolecular cycloisomerization of the at least one enyne grouping include the use of a suitable solvent.

33. The method of claim 32, wherein the solvent is 2-methyltetrahydrofuran.

34. The method of claim 26, wherein the conditions for the intramolecular cycloisomerization of the at least one enyne grouping include using a mole ratio of substrate: catalyst of about 10:1 to about 1,000,000:1.

35. The method of claim 26, wherein the conditions for the intramolecular cycloisomerization of the at least one enyne grouping include a temperature of about 0° C. to about 120° C., for 1 hour to about 96 hours.

36. The method of claim 26, performed in a flow through reactor, with or without a solvent.

37. A composition comprising a compound of formula I, a compound of formula II, or a mixture thereof and an anion abstracting agent;

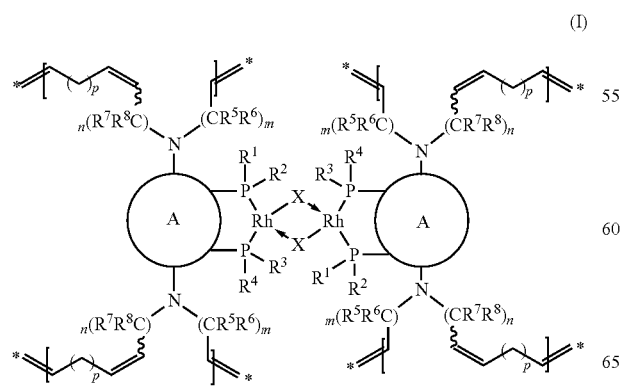

(I)

-continued

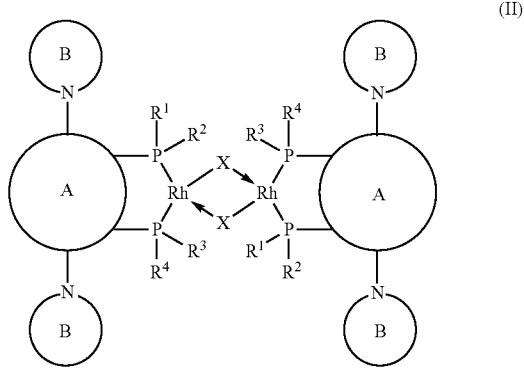

(II)

wherein $R^1$, $R^2$, $R^3$ and $R^4$ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl and halo;

Ⓐ is a binaphthyl group or a derivative of a binaphthyl group, each being unsubstituted or substituted with one or more groups independently selected from $C_{1-6}$alkyl, $OC_{1-6}$alkyl and halo;

Ⓑ is a monocyclic, bicyclic or tricylic group comprising at least one double bond and being unsubstituted or substituted with one or more groups independently selected from $C_{1-6}$alkyl, $OC_{1-6}$alkyl, halo and =O;

$R^5$, $R^6$, $R^7$ and $R^8$ are independently selected from H, $C_{1-6}$alkyl, $OC_{1-6}$alkyl and halo; or $R^5$ and $R^6$ and/or $R^7$ and $R^8$ are =O; or one of $R^5$ and $R^6$ is linked to one of $R^7$ and $R^8$ to form, together with the atoms to which they are attached and the atoms connecting them, a monocyclic, bicyclic or tricylic ring system;

$R^5$, $R^6$, $R^7$ and $R^8$ in each methylene unit is the same or different, and ∿ means the double bond attached to this bond is in the cis or trans configuration, if applicable;

m and n are, independently, an integer between and including 0 and 10;

p is an integer between and including 1 and 14; and

X is an anionic ligand.

38. A kit comprising a compound of formula I, a compound of formula II, or a mixture thereof and an anion abstracting agent, either in one composition or in separate compositions, optionally, with instructions for use;

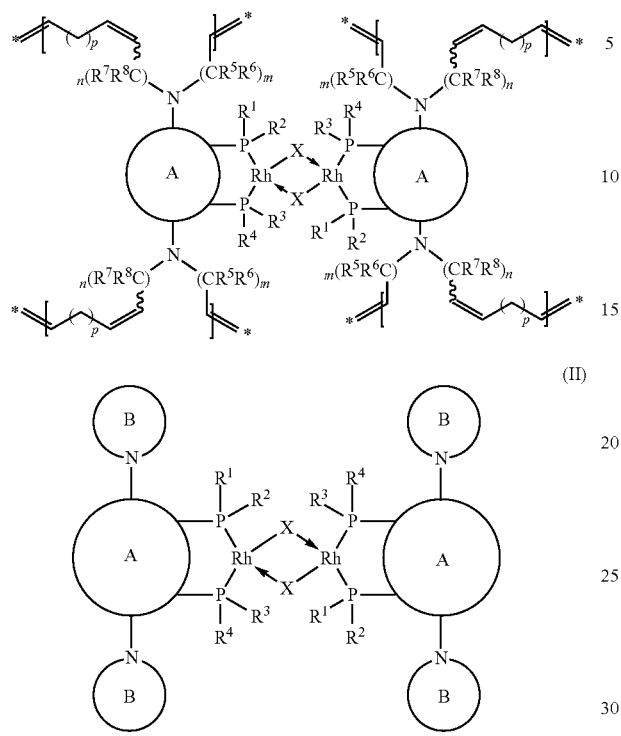

wherein

R¹, R², R³ and R⁴ are independently selected from phenyl and $C_{4-8}$cycloalkyl, the latter two groups being unsubstituted or substituted, where possible, with 1, 2, 3, 4, or 5 groups independently selected from $C_{1-6}$alkyl, $OC_{1-6}$alkyl and halo;

(A) is a binaphthyl group or a derivative of a binaphthyl group, each being unsubstituted or substituted with one or more groups independently selected from $C_{1-6}$alkyl, $OC_{1-6}$alkyl and halo;

(B) is a monocyclic, bicyclic or tricylic group comprising at least one double bond and being unsubstituted or substituted with one or more groups independently selected from $C_{1-6}$alkyl, $OC_{1-6}$alkyl, halo and =O;

R⁵, R⁶, R⁷ and R⁸ are independently selected from H, $C_{1-6}$alkyl, $OC_{1-6}$alkyl and halo; or R⁵ and R⁶ and/or R⁷ and R⁸ are =O; or one of R⁵ and R⁶ is linked to one of R⁷ and R⁸ to form, together with the atoms to which they are attached and the atoms connecting them, a monocyclic, bicyclic or tricylic ring system;

R⁵, R⁶, R⁷ and R⁸ in each methylene unit is the same or different, and ∿ means the double bond attached to this bond is in the cis or trans configuration, if applicable;

m and n are, independently, an integer between and including 0 and 10;

p is an integer between and including 1 and 14; and

X is an anionic ligand.

* * * * *